(12) United States Patent
Roy et al.

(10) Patent No.: US 7,110,489 B2
(45) Date of Patent: Sep. 19, 2006

(54) DEVICE FOR MANIPULATING A PRODUCT AND FOR PROCESSING RADIOSCOPY IMAGES OF THE PRODUCT TO OBTAIN TOMOGRAPHIC SECTIONS AND USES

(75) Inventors: Francis Roy, Les Ulis (FR); Olivier Vignon, Pontoise (FR)

(73) Assignee: Peugeot Citroen Automobiles SA, Velizy-Villacoublay (FR)

( * ) Notice: Subject to any disclaimer, the term of this patent is extended or adjusted under 35 U.S.C. 154(b) by 0 days.

(21) Appl. No.: 10/467,165

(22) PCT Filed: Feb. 13, 2002

(86) PCT No.: PCT/FR02/00554

§ 371 (c)(1),
(2), (4) Date: Dec. 12, 2003

(87) PCT Pub. No.: WO02/065110

PCT Pub. Date: Aug. 22, 2002

(65) Prior Publication Data

US 2004/0081276 A1    Apr. 29, 2004

(30) Foreign Application Priority Data

Feb. 14, 2001  (FR) .................................. 01 02014

(51) Int. Cl.
*A61B 6/02* (2006.01)
(52) U.S. Cl. ........................................ 378/20; 378/205
(58) Field of Classification Search ............ 378/20–27, 378/205, 207, 18, 17, 195, 208, 4, 19
See application file for complete search history.

(56) References Cited

U.S. PATENT DOCUMENTS 4,975,934 A    12/1990  Sauerwein et al.
6,007,243 A    12/1999  Ergun et al.
6,009,142 A *  12/1999  Sauer et al. .................. 378/15
6,072,854 A *   6/2000  Kikuchi et al. ............... 378/73
6,104,776 A *   8/2000  Oikawa ........................ 378/22
6,381,299 B1 *  4/2002  Baba et al. ................... 378/24

FOREIGN PATENT DOCUMENTS

GB    2 274 964 A    8/1994

* cited by examiner

*Primary Examiner*—Edward J. Glick
*Assistant Examiner*—Hoon Song
(74) *Attorney, Agent, or Firm*—Nicolas E. Seckel (57) ABSTRACT

The invention concerns a device produced in the form of an assembly which can be integrated in any installation (13) for radioscopy of the product and comprising means for driving the product (5) in rotation about an axis (5a) perpendicular to the tomographic section plane to be obtained, a unit controlling (15, 16) the means (14) driving the product (5) in rotation, to drive the product (5) in rotation about the axis (5a) and an image acquisition and processing unit (16) including means for automatically acquiring and storing radioscopy images of the product (5) while the product (5) is rotating, in digital form, and calculating means for processing the digital images and constructing tomographic sections using a calculating algorithm. The device enables fault controls or geometrical and dimensional controls in mechanical parts for the automotive industry such as cylinder heads.

22 Claims, 8 Drawing Sheets

DEVICE FOR MANIPULATING A PRODUCT AND FOR PROCESSING RADIOSCOPY IMAGES OF THE PRODUCT TO OBTAIN TOMOGRAPHIC SECTIONS AND USES

FIELD OF THE INVENTION

The invention relates to a device and a method of manipulating a product, and-in particular a mechanical part, and for processing images of the product obtained in a radioscopy installation in order to obtain tomographic sections of the product.

BACKGROUND OF THE INVENTION

In certain mechanical industries, and in particular in the automobile industry, new parts and new casting methods are being developed which necessitate the provision of non-destructive inspection means in order to evaluate the parts produced to new designs or obtained by new methods. In particular, it is necessary to carry out qualitative and quantitative inspections as to the material of the part in order to determined whether any defects are present as well as dimensional and geometric inspections in zones of the parts which may be inaccessible by conventional means, for example in cavities or channels inside the part.

In particular, in the case of castings of aluminium alloy or of cast iron which are used for the construction of automobiles, such as cylinder heads, crankcases, crankshafts or steering column housings, it may be necessary to carry out non-destructive inspections or dimensional inspections on batches of parts which have been obtained using new designs or by new casting methods.

In so far as castings are concerned, the defects present in the parts can be detected by X-ray radioscopy, by gamma radiography or by ultrasonic inspection. These inspection means give indications as to the presence or absence of defects in the part, but the judgement of the conformity of the part and the soundness of its material is above all qualitative.

The geometric and dimensional inspections must be carried out in a destructive manner when it is a question of checking the shapes and dimensions of internal portions of the parts. In this case parts taken from manufacture are cut in such a way as to reveal the elements to be inspected and conventional dimensional measurement tools such as callipers or micrometers are used.

In order to obtain virtual images of sections of a mechanical part, it is known to use industrial tomography devices. Such devices including a radioscopy installation, for example using X-rays, means for relative displacement of the mechanical part in rotation with respect to the radioscopy installation and means for utilising the images in order to obtain tomographic sections are very expensive and are difficult to integrate into a castings production environment.

All the industrial tomographic methods are based on the principle of acquisition and processing of images of the part which are obtained by radioscopy.

The radioscopy installation essentially comprises a source of radiation, for example X-rays, with sufficient power to pass through the mechanical part and a luminescent screen such as an image intensifier. The part is interposed between the radiation source and the screen in such a way that the radiation can pass through it, the intensity of the radiation being attenuated and modulated as it passes through the part as a function of the opacity or the density of the materials through which it passes. The radiation having passed through the part produces an image on the screen which is representative of the material through which the radiation has passed. Generally an analogue or digital camera makes it possible to acquire the radioscopic images formed on the screen.

In order to obtain virtual tomographic sections of the part along sectional planes which are parallel to one another, acquisition of radioscopic images of the part is effected according to a very large number of successive orientations which are obtained by making the part turn about an axis perpendicular to the tomographic sectional planes.

The radioscopic images in digitised form are processed in a calculator using algorithms which are all based on the same principle, consisting of carrying out a Radon transform with filtered back-projection of the images of the part, on the basis of which a reconstruction of the images is carried out in order to obtain the tomographic section.

At least one image is produced for each of the relative elementary rotations between the part and the radioscopy installation, followed by processing of the images in order to obtain a synogram, this intermediate image then being reconstructed in order to obtain the virtual image which constitutes the tomographic section.

The synogram is obtained by juxtaposing the lines of the images corresponding to the sectional plane in which the tomographic view is produced.

Several tomographic views may be produced corresponding to successive sections of a portion of the part in the direction perpendicular to the sectional plane in such a way as to reconstitute the shape of the part in three dimensions.

The method of scanned radioscopy which enables sections to be obtained through a body or object is used both in the industrial field and in the medical field.

In the case of the scanner for medical use, the whole of the radioscopy device is made to turn around the patient in order to produce the successive images which are utilised in order to reconstruct the tomographic sections.

In the case of inspection of industrial parts, the part is generally fixed on a manipulator for adjustment of its position and for its displacement in rotation.

In all cases, it is necessary to use expensive and cumbersome installations which are generally fixed permanently in a building reserved for inspection.

In the case where it is desired to carry out inspections of castings on samples coming from manufacture, such devices which are cumbersome, expensive and permanently installed are not suitable.

On the other hand, conventional radioscopy installations are generally available in workshops for production of parts in order to check for defects in samples of parts from manufacture.

Such installations have limited performance and in particular do not permit inspection of the soundness of the material from which the part is made in sectional planes passing through the part.

Equally, the conventional methods of radioscopy do not permit non-destructive dimensional or geometric inspections to be carried out inside the parts.

More generally, on the production lines for industrial products which may be for example parts or any other product, practical means are not usually available which enable tomographic sections of the products to be carried out.

SUMMARY OF THE INVENTION

The object of the invention, therefore, is to propose a device for manipulating a product and for processing images of the product in order to obtain virtual tomographic sections in a radioscopy installation comprising a source of radiation of sufficient power to pass through the product, a radiation-sensitive luminescent screen, a manipulator for displacement of the product interposed between the radiation source and the luminescent screen, and a camera for acquisition of radioscopic views formed on the screen, wherein this device which is of the multi-purpose type and is relatively inexpensive can be associated with any industrial radioscopy installation by simple and quick operations in such a way as to obtain tomographic sections of products and can be removed after a test run in order to be used on another radioscopy installation, possibly at another industrial site.

In order to achieve this object, the manipulating and processing device according to the invention is produced in the form of an assembly which can be integrated into any radioscopy installation, comprising:

a means for displacement of the product in rotation about an axis perpendicular to the tomographic sectional plane to be obtained, fixed on the manipulator, the manipulator having means for precise adjustment of the centring of the axis of rotation of the product relative to a detector formed by the screen and the camera, a unit for control of the displacement of the product making it possible to turn the product about the axis of rotation with highly precise angular positioning, a unit for acquisition and processing of images having automatic means for acquisition and storage of radioscopic images of the product, during displacement of the product in rotation, which are connected to the camera and to the means for control of the displacement of the part in rotation and automatic calculating means for the processing of the radioscopic images in digital form and the construction of tomographic sections using an algorithm for calculation and marking of the position of the axis of rotation of the product.

BRIEF DESCRIPTION OF THE DRAWINGS

In order to aid understanding of the invention a description will now be given, by way of example with reference to the accompanying drawings, of a manipulating and processing device according to the invention and use thereof in order to obtain virtual tomographic sections of an automobile part and in particular a cylinder head.

DETAILED DESCRIPTION OF PARTICULAR EMBODIMENTS

Figure 1A:
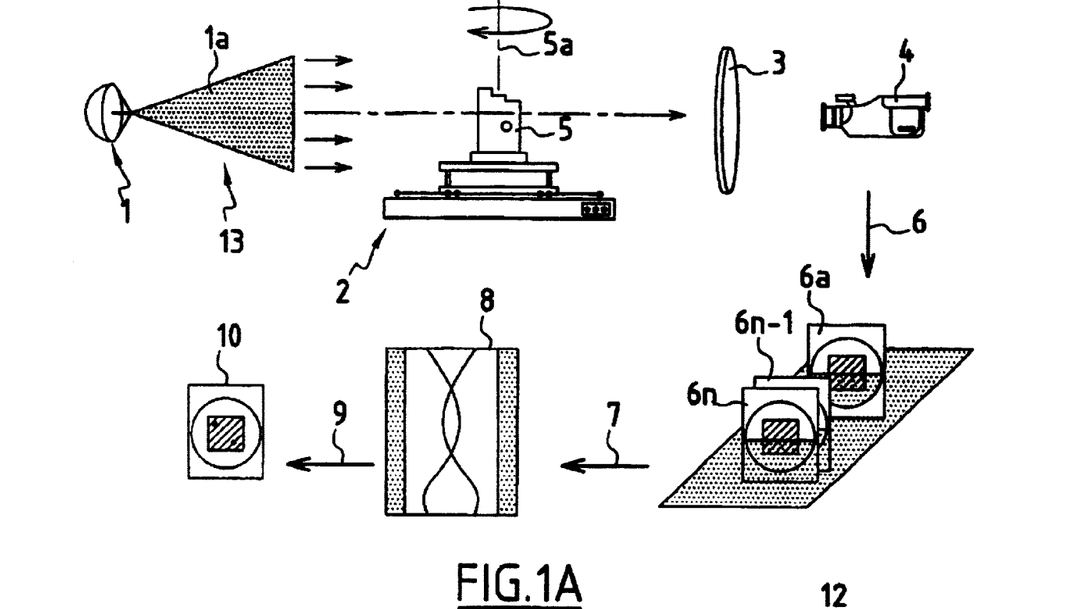
FIG. 1A is an explanatory diagram of the operation of an installation for producing tomographic sections of a part, in the form of a scanned radioscopy installation.

In FIG. 1A an installation for radioscopy of mechanical parts of the conventional type is shown which comprises an X-ray source 1, a manipulator assembly 2, a luminescent screen 3 and a camera 4.

The mechanical part 5 is fixed on the manipulator which makes it possible for the position of the part 5 to be adjusted and for the part 5 to be made to turn about an axis 5$a$.

The X-ray source 1 produces a beam of photons 1$a$ directed in such a way as to pass through the mechanical part 5 which attenuates the radiation more or less according to the density of the zones through which the radiation passes.

After the beam 1$a$ has passed through the part 5 it forms on the luminescent screen 3, which is constituted for example by an image intensifier, a radioscopic image which can be acquired totally or partially by the camera 4.

The manipulator 2 has a device for setting the part in rotation continuously or step by step, which makes it possible to obtain successive images of the part at different orientations. Each of the successive images 6$a$, . . . , 6$n$–1, 6$n$ may be obtained at an angle of orientation of the part which varies in the course of a rotation of the part, for example on a turn or a half-turn, by angular step of small amplitude (for example 1°).

For example, in the case where the part is made to go through one complete turn with a radiographic view produced at all the degrees, n=360, such that 360 successive images are produced as shown schematically by the references 6$a$ to 6$n$ in the lower part of FIG. 1.

Each of the images 6$a$, . . . , 6$n$ is digitised and introduced into a calculator in such a way as to enable the processing of the images symbolised by the arrow 7 in FIG. 1.

The radioscopic images of the part correspond to a slice of the part in the vertical axial direction 5$a$. The plane of the tomographic section of the part to be produced, which is a transverse plane perpendicular to the axis 5$a$ of the part, is located at a certain height inside the slice shown at different orientations in the images 6$a$ to 6$n$.

The images 6$a$ to 6$n$ have, according to their height, a certain number of lines, the number defining the sharpness of the radioscopic image.

One of the lines of the image corresponds to the radioscopic representation of the sectional plane of the part 5.

During the rotation of the part, views of the sectional plane are produced which are always represented by the same line of the images 6a to 6n.

The processing 7 of the images consists of taking and juxtaposing the lines corresponding to the sectional planes on each of the images 6a to 6n in order to obtain a synogram 8 having n lines, for example three hundred and sixty lines each constituted by a particular line, for example the line 288, of one of the images.

On the basis of the synogram 8 a reconstruction of the image of the part is effected in order to obtain the image 10 which is a virtual transverse tomographic section of the part.

The scanned radioscopy installation as shown in FIG. 1 is a complex installation which comprises, in addition to the components shown in FIG. 1, means for processing the images of the camera in order to carry out the processing represented by the arrow 7 and, on the basis of the synogram 8, the reconstruction of a tomographic section 10 of the part.

The reconstruction of the images on the basis of the synogram is carried out with an algorithm using a Radon transform with filtered back-projection, that is to say a transformation of a projection of the image followed by filtering of the image and inverse transformation in order to effect spreading of the elements of the image and reconstruction of the virtual section.

Figure 1B:
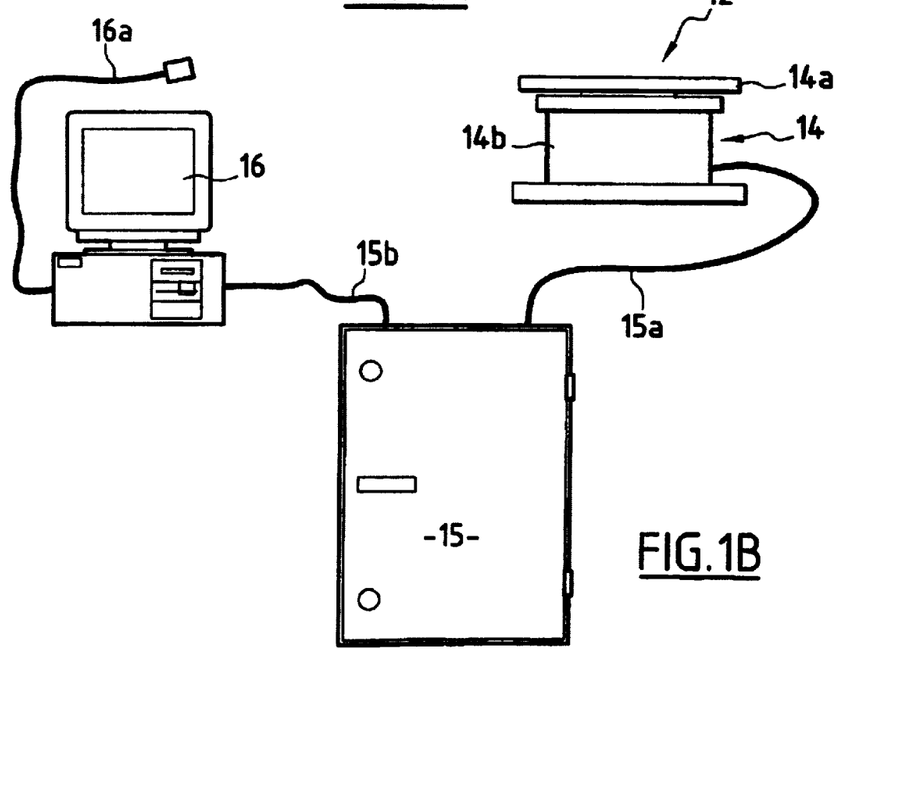
FIG. 1B is a schematic representation of a manipulating and processing device according to the invention.

FIG. 1B shows a device for manipulating parts and for processing images according to the invention, designated as a whole by the reference numeral 12 and produced in the form of a module which can be integrated in a few minutes into an industrial radioscopy installation of conventional type in order to effect tomographic sections of parts.

The device 12 includes a means 14 for displacement in rotation of a part fixed on a turntable 14a of the displacement means 14, a unit 15 for control of the rotation of the turntable and of the part, and a microcomputer 16.

The turntable 14a is driven in rotation by a motor disposed in a tubular casing 14b of the displacement means 14. The control unit 15 may be provided in the form of an electrical equipment box.

The elements which make up the device 12 according to the invention will be described in greater detail below, in particular with regard to their functions, with reference to FIGS. 2A and 4.

The electrical equipment box 15 is connected to an electronic module for control of the motor of the displacement means, for example by a first cable 15a, and to the microcomputer 16, for example by a second cable 15b.

The microcomputer 16 also has a connecting element 16a, for example a cable provided with a connector, enabling the microcomputer to be connected to the detector of a radioscopy installation.

The microcomputer 16 ensures the processing of the images and the control of the displacements in rotation of the turntable 14a of the displacement means by way of the electrical equipment box 15.

Figure 2A:
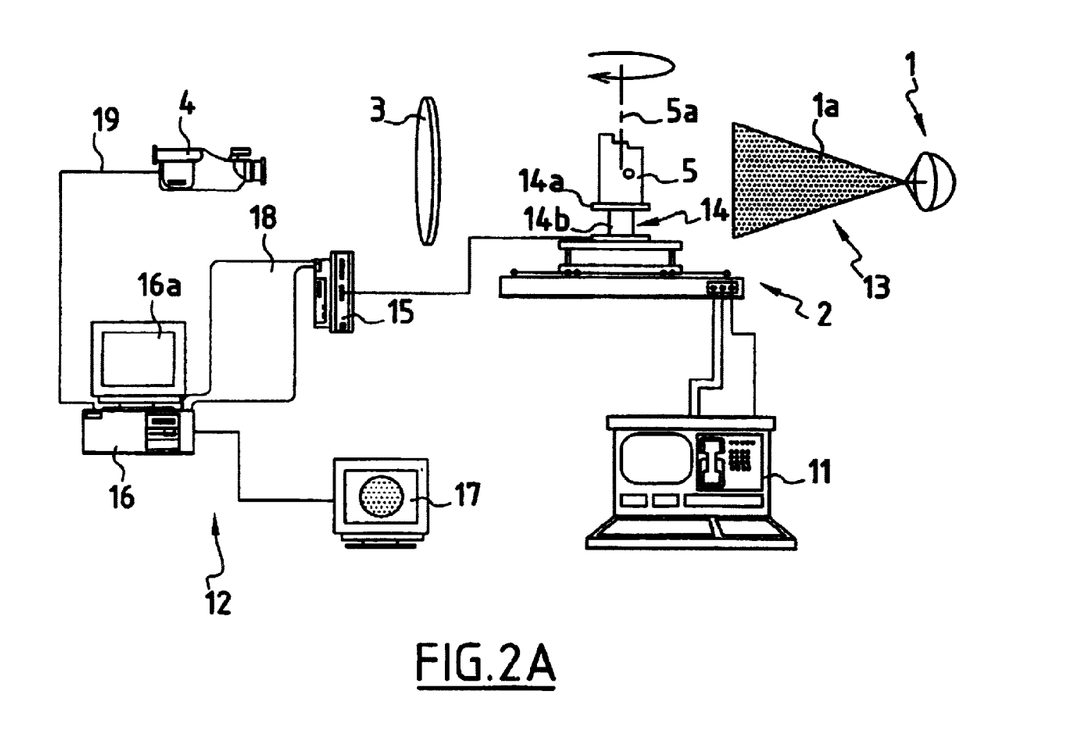
FIG. 2A is a schematic representation of a radioscopy installation with which is associated a manipulating and processing device according to the invention.

The device 12 as shown in FIG. 1B is produced in modular form and can be installed and connected to an industrial radioscopy installation is a few minutes, FIG. 2A shows a device which enables scanned radioscopy to be carried out on a mechanical part, using a conventional radioscopy installation and a manipulating and processing device according to the invention, as shown in FIG. 1B. This device is produced in the form of a multipurpose assembly which can be associated with any type of installation for radioscopy of a mechanical part in order to produce virtual tomographic sections of the mechanical parts.

The conventional installation for radioscopy of the mechanical part with which the device according to the invention is associated has components which are used in any radioscopy installation, these elements being designated by the same reference numerals as the elements of the scanned radioscopy installation shown in FIG. 1A.

These components include in particular a source of X-rays 1 producing a beam of photons 1a, a manipulator 2 for the displacements of the part 5, a luminescent screen 3 such as an image intensifier and a camera, for example a digital camera.

The manipulator 2 can be controlled from a terminal 11 in such a way as to be capable of displacing the part 5 in two directions X and Y of a horizontal plane and possibly in a vertical direction Z, and of adjusting the position of the part with respect to the beam 1a of the X-ray source 1.

This positioning of the part makes in possible in particular to obtain images of a slice of the part 5 in its vertical direction 5a in which the tomographic sectional plane is located perpendicular to the axis 5a of the part. According to the invention, the displacements of the part by the manipulator 2, controlled by the terminal 11, also permit centring of the axis 5a of the part about which the part must be made to turn by one turn or by a fraction of a turn in order to obtain the different radioscopic images, with respect to the detector consisting of the screen 3 and the camera 4, in such a way as to achieve the integration of the device according to the invention into the radioscopy installation.

A radioscopy installation 13 comprising the source 1, the manipulator 2, the screen 3 and the camera 4 makes it possible to obtain the radioscopic image of a slice at least of the part 5 in analogue or digital form, depending upon the type of camera 4.

Such a conventional radioscopy installation 13 makes it possible for example to make a non-destructive check for manufacturing defects in a mechanical part.

The only requirement concerning the radioscopy installation is that the power of the X-ray source should be sufficient in order to obtain a beam of photons 1a which can pass through the part 5.

In the case where the radioscopy installation 13 is used for the production of tomographic sections on a mechanical part such as a cylinder head of an automobile, a source having a power of 260 to 450 kV is used, for example. This power currently used in conventional radioscopic installations makes it possible to obtain images which can be easily used for the processing and the reconstruction of virtual tomographic sections.

A radioscopy installation such as 13, used for non-destructive checks on parts of a manufacturing run, does not include means permitting the acquisition of successive radioscopic images, the processing of these successive images and the reconstruction of tomographic sections, like the installation shown in FIG. 1A, in which the means necessary for scanned radioscopies are not shown; these means integrated into the installation in the form of fixed components are complex and expensive.

FIG. 2A shows a device for manipulating and processing images according to the invention, designated in a general manner by the reference numeral 12, which constitutes a multipurpose assembly which can be associated with any conventional radioscopy installation in which the X-ray source 1 has a sufficient power. The device 12 according to the invention, which is analogous to the device shown in FIG. 1B, includes a means for displacement in rotation 14 of the part 5 about its axis 5a, a unit for control 15 of the rotation of the part 5 by way of the drive means 14 and a calculator 16 consisting of a microcomputer of a type adapted to the processing and the reconstitution of the tomographic images.

The device 12 according to the invention can also include a screen 17 for visualisation of the radioscopic images of the part 5 connected to the microcomputer 16.

The drive means for displacement in rotation of the part 5 includes in particular a turntable 14*a* on which the part 5 can be fixed in an adjustable position and a torque motor 30 disposed in the interior of a tubular casing 14*b* in such a way as to engage with the turntable 14*a* in order to set it in rotation about a vertical axis of rotation 5*a* along which the axis of rotation of the part 5 is placed.

The manipulator 2 of the radioscopy installation which may be formed by an elevating table with crossed movements comprises a horizontal upper table on which is fixed the support 14*b* for the drive means for displacement in rotation 14.

In a preceding phase of adjustment of the device which will be described with regard to FIGS. 2B and 2C, the axis of rotation of the turntable 14*a* is precisely marked on the image obtained from the screen 3 and the camera 4 of the detector of the radioscopy installation.

In fact, the algorithm for reconstruction of the tomographic sections to be produced, which is used within the framework of the invention and which enables these sections to be produced by virtue of the device according to the invention associated with a conventional industrial radioscopy installation, necessitates a knowledge of the physical axis 5*a* of rotation of the turntable 14*a* and of the part 5 with respect to the centre of reconstruction of the tomographic images.

Figure 2B:
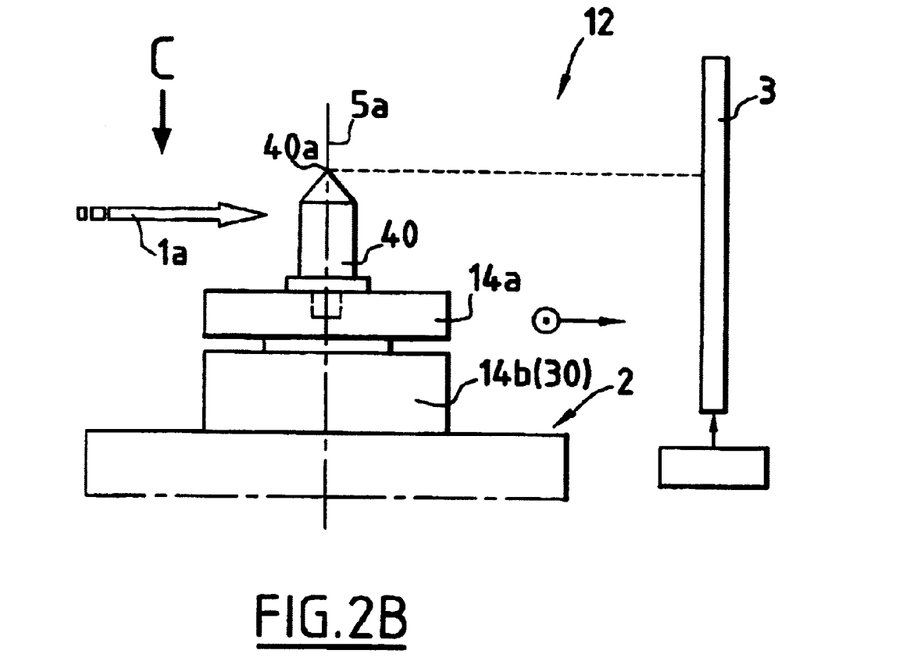
FIG. 2B is a schematic view in elevation of the device according to the invention during a phase prior to marking of the axis of rotation of the part.
Figure 2C:
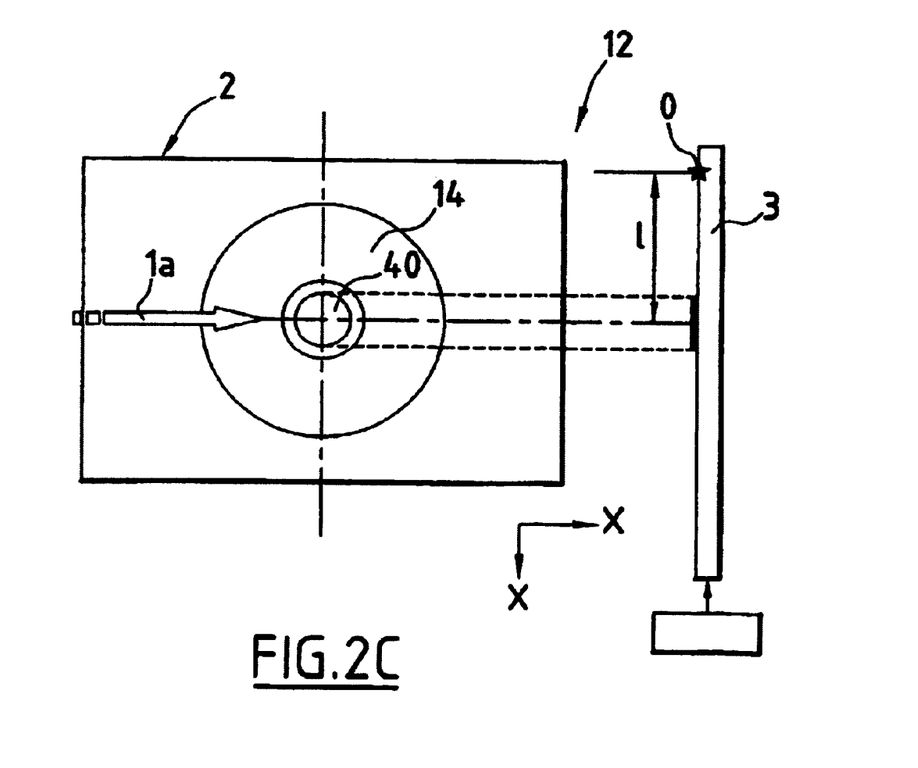
FIG. 2C is a plan view according to C in FIG. 2B.

As shown in FIGS. 2B and 2C, a rod 40 of very dense material (in so far as the absorption of the X-rays is concerned), for example made from brass, having a tip 40*a* is fixed along the axis 5*a* of the turntable 14*a* (in the absence of the part 5) in such a way that the tip 40*a* of the rod is situated on the axis 5*a*.

The beam of X-rays 1*a* is directed onto the rod 40 and thus a radioscopic image of the rod is produced on the detector (screen 3 and camera 4). As shown in FIG. 2C, the value l (expressed in pixels and with a precision of more or less 1 pixel) of the distance of the projection of the tip 40*a* on the radioscopic image is recorded, at a point of origin O, in the horizontal direction X. The origin 0 may be the origin or centre of the reference mark in which the calculation for reconstruction of the tomographic sections is carried out. The value l serves as input data for the code for calculation for reconstruction of the tomographic sections.

Figure 10:
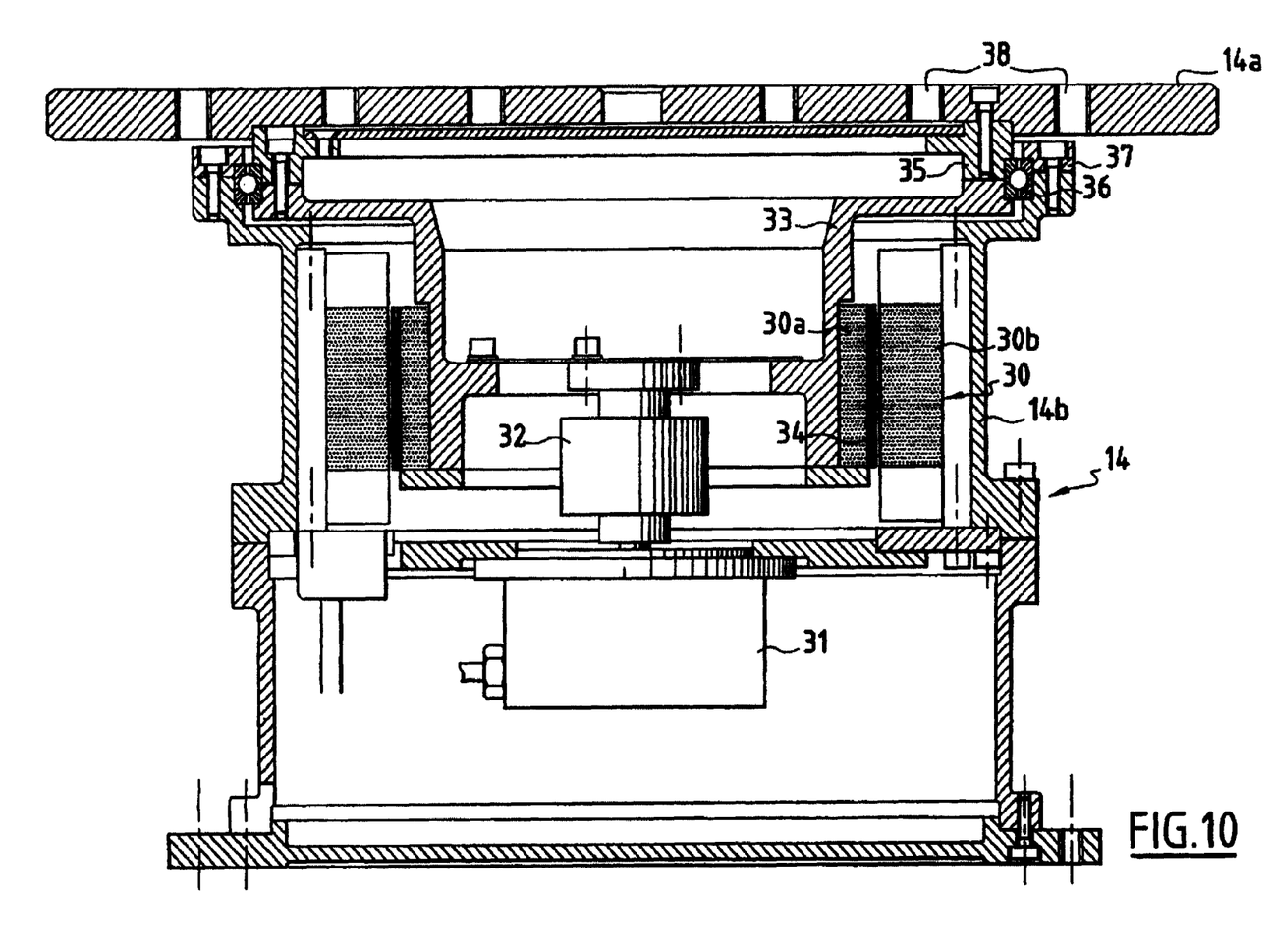
FIG. 10 is a view in partial axial section and in elevation of the means for displacement of parts in rotation of the device according to the invention.

Preferably, as shown in FIG. 10, the means for displacement in rotation 14 of the part 5 which must make it possible in particular to effect step-by-step displacements of small amplitude, with extremely precise marking of angular position, may consist of a torque motor 30 of which the rotor 30 has permanent magnets and the stator 30*b* has windings which are supplied under electronic control in order to obtain the required rotations of the turntable 14*a*, the precise position of the turntable 14*a* in orientation being measured by a high-precision encoder 31 associated with the motor 30, in the interior of the tubular support 14*b* of the displacement means 14.

The rotor 30*a* of the torque motor 30 has a rotor support 33 of tubular shape on which the permanent magnets 34 are fixed. The windings of the stator 30*b* are fixed on a stator support which is integral with the tubular support 14*b* for the means for driving in rotation 14, opposite the permanent magnets 34, providing a narrow gap.

The turntable 14*a* of the means for driving in rotation 14 is rigidly joined to the rotor support 33 on which it is fixed by way of a first rim 35. In this way a direct transmission of torque is obtained between the rotor and the turntable 1*a* and the use of mechanical transmission means, which may exhibit some play after a certain period of operation, is avoided. This improves the conditions of displacement in rotation of the turntable 14*a* and the precision of the successive positions thereof. The turntable 14*a* is mounted so as to rotate on the tubular support 14*b* by way of a single rolling bearing 36 of which the inner ring is fixed between the rotor support 33 and the first rim 35 and the outer ring is fixed between a second rim 37 and the tubular support 14*b*, in such a way that the bearing 36 and the motor 30 are coaxial. The rotating part of the encoder 31 is connected to the rotor support 33 by a coupling 32.

The windings of the stator 30*b* are supplied by electronic means of a variator 15 in such a way as to make the rotor 30*a* and the turntable 14*a* turn step by step or continuously. The encoder 31 is also connected electrically to the variator and through it to the microcomputer 16. The encoder 31, which has a very large number of measurement positions per turn (for example 36,000 positions/turn), makes it possible on the one hand to determine the angular position of the turntable 14*a* and of the mechanical part 5 with a very high degree of precision and on the other hand to refine the stopping positions of the turntable 14*a* by way of the variator 15 supplying the windings of the stator which has a regulation loop.

The turntable 14*a* has threaded holes 38 distributed over its surface to enable the fixing of parts 5 of various shapes.

The tubular support 14*b* is produced in two parts in order to permit the mounting of the means for driving in rotation 14.

The electronic means for controlling the torque motor and for measuring the position of the turntable 14*a* are connected by a ring 18 consisting of optical fibres to the microcomputer 16 in such a way that it is possible to adjust the conditions of displacement in rotation of the part 5 from the microcomputer 16 and to synchronise the radioscopic shot by way of the camera 4 which is also connected to the microcomputer 16, with the positions of the part 5 in rotation about its axis 5*a* defined and marked in a precise manner.

In the case where the camera 4 is a digital camera the digital data of the image are transmitted directly to the microcomputer 16, and in the case where the camera 4 is an analogue camera an analogue/digital conversion unit is used which is associated with the inputs of the microcomputer 16.

Figure 3:
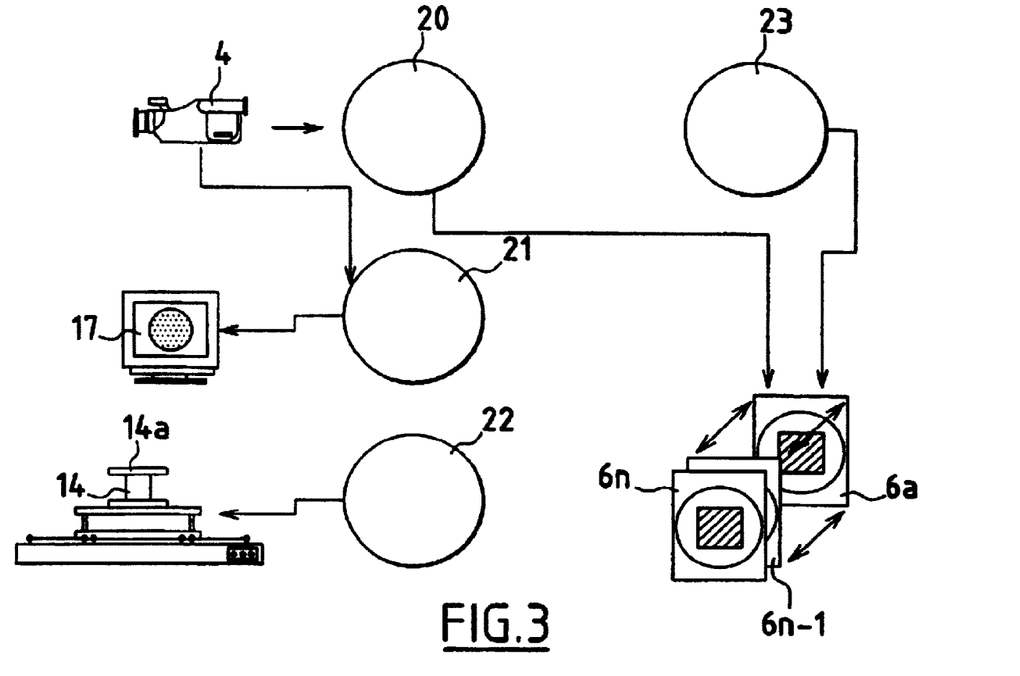
FIG. 3 shows part of the components of the installation shown in FIG. 2 and their operation during the acquisition of radioscopic images of the mechanical part.

FIG. 3 shows the camera 4 for acquisition of the radioscopic images on the luminescent screen 3, a display screen 17 and the manipulator 2 on which is fixed the means for displacement in rotation 14 with the turntable 14*a*.

FIG. 3 also shows, in the form of circles 20, 21, 22 and 23, the functions carried out by the camera 4, the display screen 17 and the means for displacement in rotation 14 of the manipulator 2 during the acquisition of the radioscopic images of the part 5 under the control of the microcomputer 16.

The functions are as follows:

20: collection of the successive images 6*a*, . . . , 6*n* by the camera 4 during the rotation of the part;

21: display of images on the display screen 17;

22: control of the means for displacement in rotation 14 of the manipulator 2 in synchronism with the taking of radioscopic shots;

23: calculation by the microcomputer 16 of digital images corresponding to successive shots taken in a position of angular orientation of the part 5.

It may be of interest to average at least two images produced in each angular position determined in order to eliminate disturbances of the images of a random or periodic type.

Figure 4:
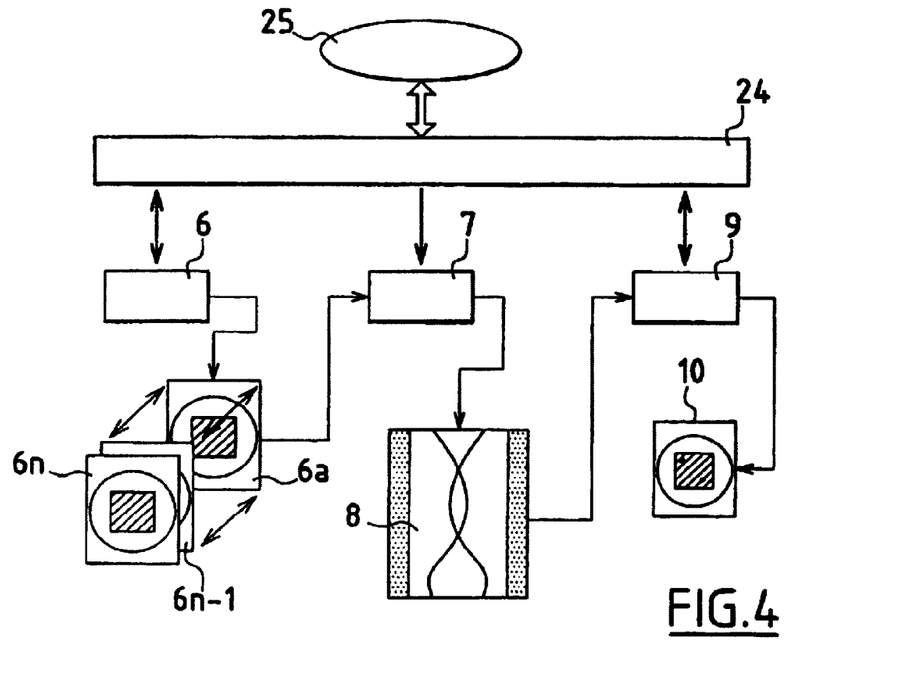
FIG. 4 is a functional diagram of an operation of acquisition, processing and reconstruction of tomographic images using the device according to the invention.

FIG. 4 shows, in the form of rectangles 6, 7 and 9, the different steps of the method of scanned radioscopy implemented by the device according to the invention which correspond respectively to the steps of acquisition 6 and of processing 7 of images and of reconstruction of a tomographic section 9, these steps being represented by arrows on the diagram of FIG. 1 relating to the use of any scanned radioscopy installation.

The acquisition step 6 was described with regard to FIG. 3 concerning the functions implemented by the different components of the installation within the framework of the use of an installation according to the invention.

The processing step 7 consists of producing a synogram 7 from the lines o the images 6a, . . . , 6n corresponding to the tomographic sectional plane to be produced, and step 9 is the step of reconstruction by Radon transform which was described above.

A rectangle 24 represents the user interface of the microcomputer 16 which is accessible to the operator 25 of the method in order to fix the parameters of the method and to control this different steps.

The processing of the images 6a, . . . , 6n in order to constitute the synogram 8 can be carried out immediately after the acquisition of an image and before the acquisition of a following image, the synogram 8 being obtained progressively during the rotation of the part, for example over a complete turn.

The rotation of the part can be carried out step by step or continuously.

Generally, the acquisitions and the reconstructions of the tomographic sections can be carried out in real time or deferred or with only the reconstruction deferred.

In order to obtain a 3D representation of a slice of the part, several synograms are produced, on the basis of radioscopic images, corresponding to several sectional planes of the slice, and the tomographic sections of the part which can be juxtaposed in order to provide the 3D representation are reconstructed.

Generally, for each of the slices of the part a plurality of synograms and a plurality of tomographic sections, at different levels, can be produced.

The operator 25 also has the use of the display screen 17 in order to check the progress of the rotation of the part and the taking of the shots during the acquisition of the images.

Figure 5:
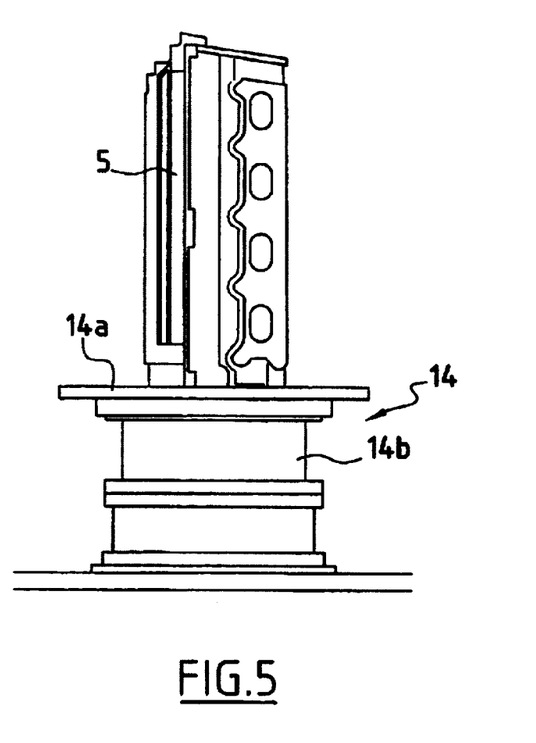
FIG. 5 is a view in elevation of a cylinder head of an automobile mounted on the means for displacement in rotation according to the invention.

FIG. 5 shows the means for displacement in rotation 14 of the part 15 which includes a support cylinder 14b and the turntable 14a driven in rotation by the controlled torque motor 30 disposed in the interior of the tubular support 14b.

The part 5 fixed on the turntable 14a on which tomographic sections are to be produced is a cylinder head which is placed in a vertical arrangement on the turntable 14a, that is to say with its longitudinal direction parallel to the line of cylinders of the vertically-placed motor.

An adjustment of the position of the cylinder head 5 on the turntable is carried out in such a way that the rotation of the cylinder head about an axis 5a merged with the axis of the turntable ensures that complete radioscopic images are obtained of the zone of the cylinder head to be observed.

In effect it is possible, as a function of the dimensions of the detector formed by the screen and the camera of the radioscopy installation, to take shots over all of the cross-section of the cylinder head or, on the contrary, over only a part of this section. The size of the observable section of the cylinder head is substantially equal to the size of the zone of acquisition of the detector.

In fact, outside the zone of the cylinder head which is situated on each of the successive images during the step-by-step rotation of the cylinder head about the axis 5a, zones exist which are situated on only a part of the images taken during the step-by-step rotation of the cylinder head, due to the fact that this cylinder had does not have a rotational shape about the axis 5a.

These external zones may be represented on the tomographic sections with less sharpness than the central zone. In all cases, the software for processing the images which is loaded into the microcomputer 16 makes it possible to produce partial tomographic sections of the parts and to reconstitute complete sections by juxtaposition of the partial sections.

Figure 6:
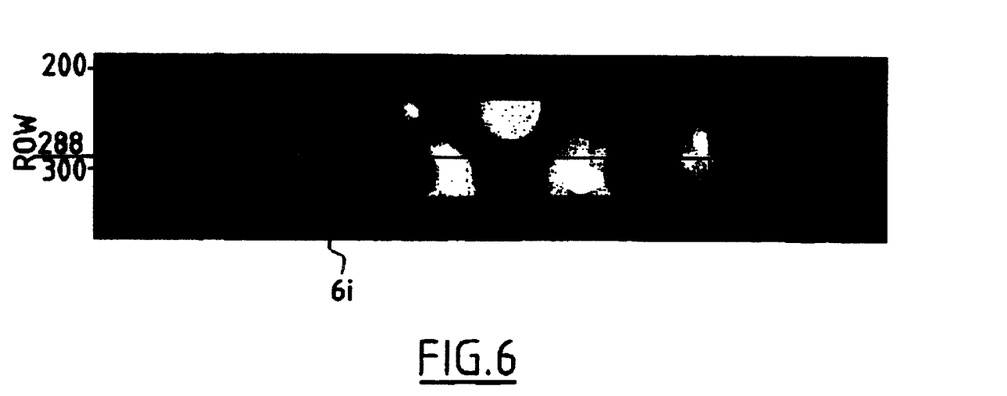
FIG. 6 is a radioscopic image of the cylinder head produced in an acquisition phase of the method using the device shown in FIG. 2.

FIG. 6 shows one of the radioscopic images 6i of the cylinder head obtained during the rotation of the cylinder head, this image corresponding to a slice of the cylinder head along its vertical axis 5a and including approximately one hundred lines of images, between the lines 230 and 330.

FIG. 6 also shows in solid lines the line 288 which is situated at the level of the tomographic section to be produced.

The manipulating and processing device according to the invention makes it possible to produce a large number of images such as 6i each corresponding to a position of acquisition of images of the cylinder head about its axis 5a, for example three hundred and sixty images can be produced in the course of one rotation about the cylinder head, each of the images being taken with an offset of 1 degree relative to the previous one. More generally, acquisitions of images can be effected in a plurality of successive positions of the part or product examined, the angle between two successive positions having any fixed value.

Each of the positions can be defined with a very high degree of precision by virtue of the encoder of the means for displacement in rotation of the turntable. It is equally possible to carry out a number of steps greater than 360 in the course of one turn, for example 3600 steps having an amplitude of one tenth of a degree.

It is equally possible to produce tomographic sections by making the cylinder head turn by half a turn or a fraction of a turn instead of a complete turn.

As indicated above, one single view of the cylinder head can be produced in a defined angular position or, again, at least two images can be produced of which an average is produced in order to eliminate disturbances.

Figure 7:
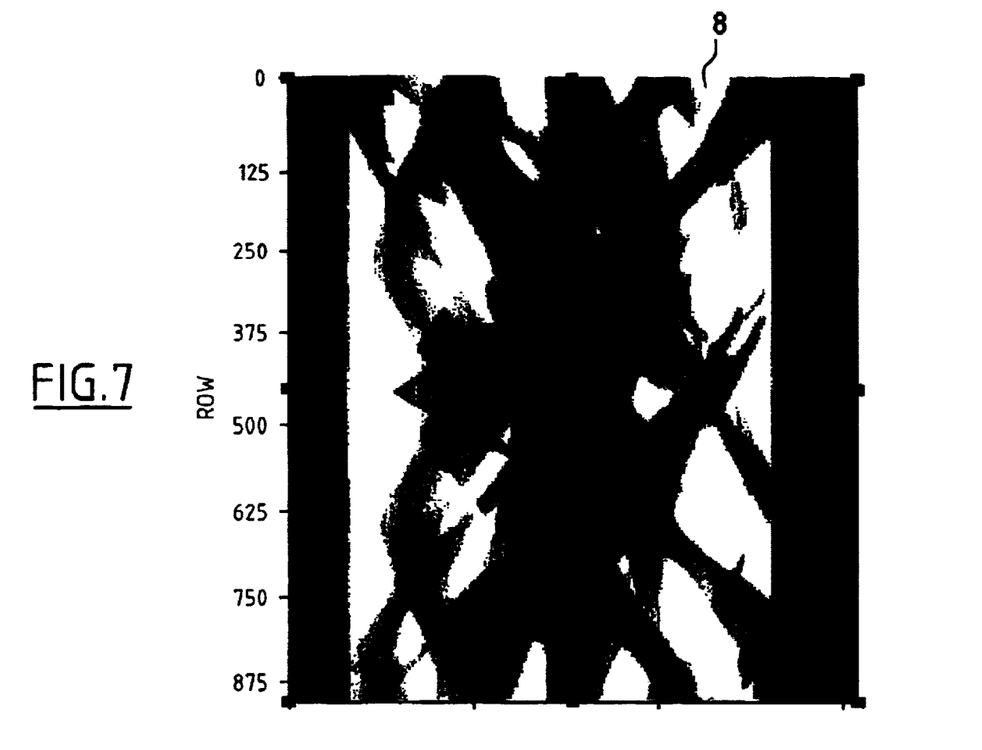
FIG. 7 is a synogram of the cylinder head corresponding to the lines of the radioscopic images at the level of a tomographic section to be produced.

On each of the images such as 6i shown in FIG. 6, the digital data relating to a line (for example the line 288) are taken and a synogram 8 such as is shown in FIG. 7 is produced which corresponds to each of the three hundred and sixty lines 288 of the radioscopic images 6i taken during the rotation of the cylinder head by one turn.

As indicated above, a tomographic section 10 can be obtained by reconstruction on the basis of the synogram 8, with possible filtering of the synogram in order to increase the precision of certain aspects of the tomographic section.

Filtering can also be carried out in the reconstruction step, after a first transform of the projection corresponding to the image.

Figure 8A:
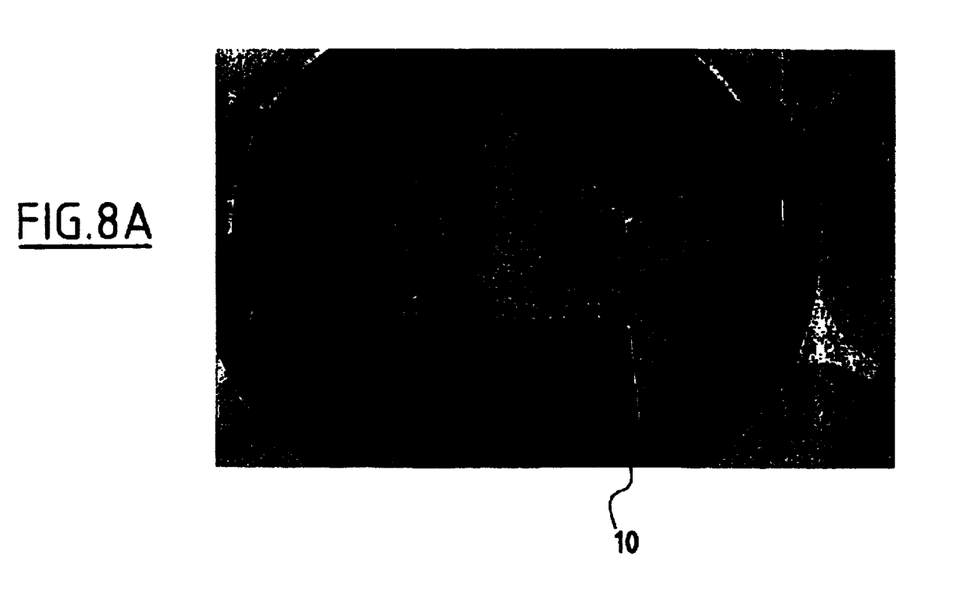
FIG. 8A is a view of a virtual tomographic section reconstituted on the screen of the processing unit of the device according to the invention.

In FIG. 8A a tomographic section 10 can be seen displayed on the screen 16a of the microcomputer 16 at the request of the operator using the scanned radioscopy device.

Figure 8B:
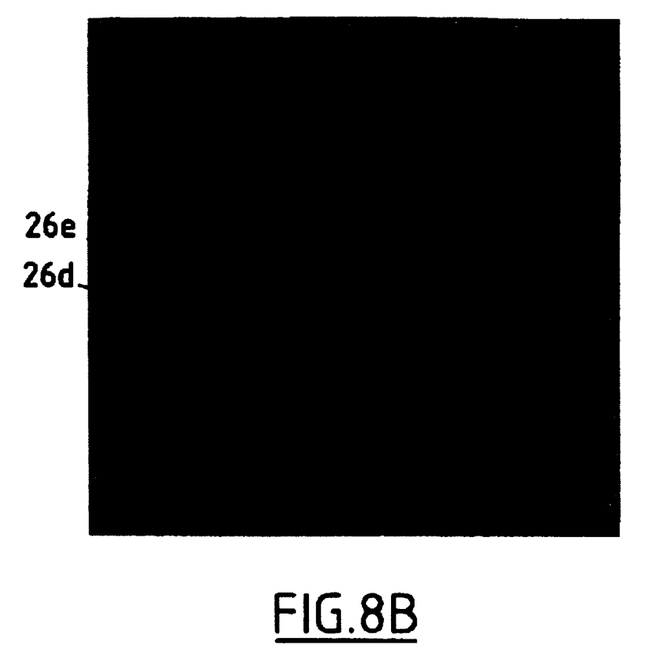
FIG. 8B is a partial view of the tomographic section showing defects in the cylinder head.

FIG. 8B shows a part of the tomographic section of the cylinder head showing the defects 26a, 26b, 26v, 26d, 26e, 26f, 26g which consist of cavities of different dimensions inside the metal of the cylinder head.

With the method according to the invention, by producing virtual tomographic sections of the part it is possible to detect defects of very small dimensions, for example a dimension of the order to $1/10^{th}$ of a millimetre.

The dimensional resolution on the reconstructed images is principally conditioned by the nature of the emission and of the radiation detection assembly. Thus it is possible to envisage detection of defects of the order of several micrometres.

Equally, using a tomographic section such as is shown in FIG. 8B it is possible to measure dimensions of portions of the part which are totally inaccessible, for example dimensions of channels or cavities inside the part with a very high degree of precision. The ratio of scale between the dimensions measured on the tomographic section and the real dimensions can be given using the length measured on the tomographic section of an element which can be measured directly on the part.

Figure 9:
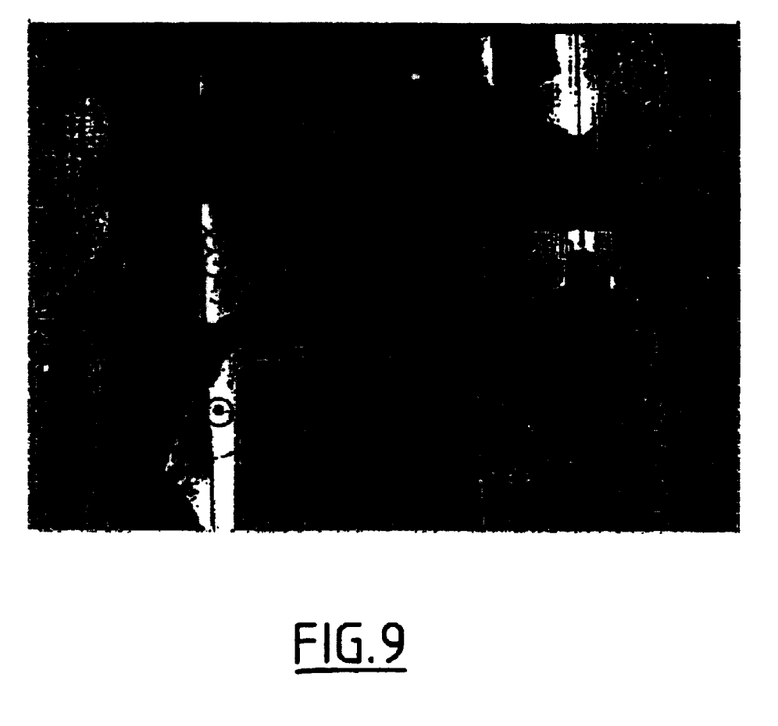
FIG. 9 is photographic view of a plane of cutting the cylinder head close to the tomographic section produced previously.

According to the prior art it used to be necessary to cut the part by machining in order to detect internal defects distributed along a cross-section or in order to measure dimensions of internal portions of the part. As can be seen in FIG. 9, showing a photographic view of a section produced by machining of the cylinder head 5 in the region of the plane of the virtual tomographic section 10 after the radiographic examination, the defects appear in a similar manner on the virtual section and on the real section.

By virtue of the device and the method according to the invention it is possible for the field of use of radioscopy to be extended easily to geometric inspection and to link the results obtained by this inspection to the data supplied by the CAD means. For example, it is possible to effect automatic drawing of parts on the basis of records on a tomographic section or to produce comparisons between real parts and parts drawn by CAD.

The method of producing tomographic sections using the device according to the invention therefore makes it possible to:

detect and quantify defects of the material of which a mechanical part is made, in a non-destructive manner;

to carry out non-destructive geometric measurements in zones which are inaccessible by conventional means;

to obtain a better knowledge of the production of the mechanical parts by more frequent non-destructive inspection;

to increase productivity by avoiding slicing parts in order to carry out destructive inspections;

to extend the field of use of radioscopy to geometric inspection in conjunction with CAD hardware and software.

The device according to the invention is totally independent of the nature of the parts or products to be inspected, with the proviso that it is associated with a radioscopy installation having a sufficiently powerful radiation source for the photon flux to pass through the part or product.

The device is also independent of the size of the product, which is useful in particular when the size of the radioscopic projection of the product is greater than the size of the detector utilised. In this case the reconstruction of the virtual tomographic section is effected inside a circle of projection inscribed in the detector.

The device for manipulation of the product and for processing of the radioscopic image can be integrated into any radioscopy installation by simple adaptation operations.

In particular, the device can be used in combination with a radioscopy installation situated in an industrial radioscopy environment, such as a foundry.

The invention is not strictly limited to the embodiment which has been described.

Thus the means for displacement in rotation of the product may be different from the turntable driven by a torque motor which has been described. The manipulator which ensures the displacement of the product may comprise only the means for displacement in rotation of the part. The means for processing and reconstruction of the tomographic images can use any type of automatic calculating machine and any type of software.

The invention applies not only to the radioscopic inspection of parts used in automobile construction such as cylinder heads, steering column housings, crankcases or crankshafts produced by casing of aluminium alloy or of cost iron, but also to any product on which a geometric or dimensional inspection or even a quality inspection of the material. However, the device and the method according to the invention apply above all within the framework of the design of parts or products of a novel type or manufactured by a novel method.

The device according to the invention makes it possible to equip not only X-ray radioscopy installations but also other radioscopy installations using any type of radiation or any inspection installation, for example using neutron fluxes. Amongst other things, the device according to the invention can be integrated into a synchrotron cell.

If the manipulator of the radioscopy installation already has a means for mechanical displacement in rotation, it is possible to use it for the displacement of the product during the implementation of the invention and to avoid replacement thereof by a means specific to he device according to the invention. This displacement means is then integrated into the device according to the invention.

Generally, the source of radiation of the radioscopy installation is a source which emits X-rays, neutrons or any other type of radiation which can be attenuated as it passes through the product observed.

The invention claimed is:

1. Device for manipulating a product and for processing images in order to obtain virtual tomographic sections of the product, comprising:

a radioscopy installation comprising a source of radiation of sufficient power to pass through the product, a radiation-sensitive luminescent screen, a manipulator for displacement of the product interposed between the radiation source and the luminescent screen, and a camera for acquisition of radioscopic images formed on the screen, wherein the manipulator is an elevating table having mobility in two crossed directions for the displacement of the product in two directions of a horizontal plane said elevating table being controlled by a terminal for centering the product with respect to a detector formed by the screen and the camera, said device further comprising an assembly which is separately removable from the radioscopy installation, said assembly comprising:

a means for displacement of the product in rotation about an axis perpendicular to the tomographic sectional plane to be obtained, fixed on the manipulator, a unit for control of the displacement of the product making it possible to turn the product about the axis of rotation with highly precise angular positioning, a unit for acquisition and processing of images having automatic means for acquisition and storage of radioscopic images of the product, during displacement of the product in rotation, which are connected to the camera and to the unit for control of the displacement of the product in rotation and automatic calculating means for the processing of the radioscopic images in digital form and the construction of tomographic sections using an algorithm for calculation and marking of the position of the axis of rotation of the product.

2. Device as claimed in claim 1, wherein the radiation source is a source which emits X-rays, neutrons or any other radiation which is attenuated as it passes through the product.

3. Device as claimed in claim 2, wherein the radiation source is a generator of X-rays.

4. Device as claimed in claim 1, wherein the means for displacement of the product in rotation consists of a turntable mounted so as to turn about an axis on a tubular support by way of a single bearing and driven in rotation by a torque motor of which the rotor with permanent magnets is directly joined to the turntable, the control unit of the means for driving in rotation consisting of an electronic unit for control of the torque motor of the means for driving in rotation connected to an encoder for measurement of the angular position of the rotor and of the turntable for the adjustment of stopping positions of the rotor of the motor and of the turntable or of positions of acquisition of images.

5. Device as claimed in claim 1, wherein the unit for acquisition and processing of images comprises a microcomputer connected to the camera in order to receive radioscopic images in digital form and comprising calculation software for the processing of the images in digital form in order to draw up at least one sinogram on the basis of at least one line of each of the radioscopic images and to reconstitute at least one tomographic section on the basis of at least one synogram with the aid of a calculating algorithm using a Radon transform.

6. Device as claimed in claim 5, wherein the microcomputer is connected to a variator of the means for displacement in rotation of the product in order to synchronise the taking of radioscopic images on the luminescent screen by the camera with step-by-step displacement in rotation of the product in order to take at least one shot between each of the successive steps of displacement in rotation of the product.

7. Device as claimed in claim 5, wherein it further comprises a screen for display of the radioscopic images which is connected to the microcomputer.

8. Method of detecting defects in the material of a product, comprising:
providing a device as claimed in claim 1, manipulating the product for displacement of the product interposed between the radiation source and the luminescent screen, and
acquiring radioscopic images of the product.

9. Method of carrying out a geometric or dimensional inspection of portions of a product which are not accessible from the exterior, comprising:
providing a device as claimed in claim 1,
manipulating the product for displacement of the product interposed between the radiation source and the luminescent screen, and
acquiring radioscopic images of the product.

10. Method of inspecting mechanical parts of one of the following types: casting for the automobile industry, cylinder head, crankcase, crankshaft, steering column housing, comprising:
providing a device as claimed in claim 1,
manipulating the mechanical parts for displacement of the product interposed between the radiation source and the luminescent screen, and
acquiring radioscopic images of the mechanical parts.

11. Device as claimed in claim 1, wherein the displacement means is removably fixed on the manipulator.

12. Device as claimed in claim 1, wherein the control unit is not mounted on the radioscopy installation.

13. Method of manipulating a product and processing radioscopic images of the product in order to obtain tomographic sections of the product, using a radioscopy installation comprising a source of radiation of sufficient power to pass through the product, a radiation-sensitive luminescent screen, a manipulator interposed between the radiation source and the luminescent screen for displacement of the product, and a camera for acquisition of radioscopic images formed on the luminescent screen, in which the product is made to turn about the axis perpendicular to the plane of the tomographic section to be produced, with highly precise angular positioning of the product about the axis, for each of the successive positions of the product in rotation at least one radioscopic acquisition is carried out in order to obtain a radioscopic image of the product in digital forum, each of the digital images obtained in the successive positions of the product in rotation is processed in order to extract at least one line of the radioscopic image and to constitute at least one synogram on the basis of the lines extracted from the digital images of the product, and at least one tomographic section of the product is produced by reconstruction from the at least one synogram, wherein prior to setting the product in rotation a rod made from dense material and having a tip is placed along an axis of rotation of a turntable for displacement in rotation of the product, in such a way that the tip is on the axis of rotation of the product, a radioscopic image of the rod is produced and a distance of the projection of the tip of the rod on the radioscopic image with respect to a reference point is recorded, the distance being used as input data of code for calculation for reconstruction of the tomographic section.

14. Method as claimed in claim 13, wherein the acquisition of at least two radioscopic images is effected for each of the successive positions of acquisition in rotation of the mechanical part, and that an average age is calculated on the basis of the at least two radioscopic images obtained at each angular position for acquisition of the product.

15. Method as claimed in claim 13, wherein a plurality of lines is extracted from each of the radioscopic images in a slice of the product extending along the axis in order to obtain a plurality of synograms, and that a plurality of tomographic sections of the slice of the product are reconstructed on the basis of each of the synograms of the plurality of synograms in such a way as to obtain a representation a representation of the slice of the product in three dimensions.

16. Method as claimed in claim 13, wherein the product is made to turn about the axis by a complete turn or by a fraction of a turn and that a radioscopic shot is taken in each of a plurality of positions of acquisition of images of the product.

17. Method as claimed in claim 16, wherein the angle between two successive positions of acquisition has a predetermined fixed amplitude.

18. Method as claimed in claim 13, wherein the acquisition of radioscopic images of only a portion of the product is carried out in each of the successive positions of acquisition of the product, each of the images of a portion of the product having the maximum dimension of acquisition of an image detector formed by the luminescent screen and the camera.

19. The method as claimed in claim 13, comprising detecting the presence or not of defects in the material of the product.

20. The method as claimed in claim 13, comprising carrying out a geometric or dimensional inspection of portions of the product which are not accessible from the exterior.

21. The method as claimed in claim 13, comprising inspecting mechanical parts of one of the following types: casting for the automobile industry, cylinder head, crankcase, crankshaft, steering column housing.

22. Device for manipulating a product and for processing images in order to obtain virtual tomographic sections of the product in a radioscopy installation comprising a source of radiation of sufficient power to pass through the product, the radioscopy installation comprising a radiation-sensitive luminescent screen, a manipulator for displacement of the product interposed between the radiation source and the luminescent screen, and a camera for acquisition of radioscopic images formed on the screen, produced in the form of an assembly which can be integrated into any radioscopy installation comprising:

a means for displacement of the product in rotation about an axis perpendicular to the tomographic sectional plane to be obtained, fixed on the manipulator, a unit for control of the displacement of the product making it possible to turn the product about the axis of rotation with highly precise angular positioning, a unit for acquisition and processing of images having automatic means for acquisition and storage of radioscopic images of the product, during displacement of the product in rotation, which are connected to the camera and to the unit for control of the displacement of the product in rotation and automatic calculating means for the processing of the radioscopic images in digital from and the construction of tomographic sections using an algorithm for calculation and marking of the position of the axis of rotation of the product, wherein a rod made from dense material and having a tip is placed along an axis of rotation of the unit for control of the displacement of the product, in such a way that the tip is on the axis of rotation of the product.

* * * * *